United States Patent [19]

Fürst et al.

[11] 4,155,918
[45] May 22, 1979

[54] NOVEL D-HOMOSTEROIDS

[75] Inventors: Andor Fürst, Basel; Marcel Müller, Frenkendorf, both of Switzerland; Ulrich Kerb; Rudolf Wiechert, both of Berlin, Fed. Rep. of Germany

[73] Assignee: Hoffmann-La Roche Inc., Nutley, N.J.

[21] Appl. No.: 887,161

[22] Filed: Mar. 16, 1978

Related U.S. Application Data

[63] Continuation of Ser. No. 736,282, Oct. 28, 1976, abandoned.

[51] Int. Cl.$^2$ .................... C07D 309/22; C07C 49/48
[52] U.S. Cl. ...................... 260/345.9 S; 260/345.8 R; 260/586 E; 568/823; 568/665; 568/660; 560/107; 560/194; 560/257; 546/285; 546/268
[58] Field of Search .......... 260/345.9, 586 E, 295.5 P, 260/345.8, 611 F, 611 A; 568/823; 560/107, 194, 257

[56] References Cited

U.S. PATENT DOCUMENTS

| | | | |
|---|---|---|---|
| 2,854,459 | 9/1958 | Knowles et al. | 260/586 E |
| 3,110,733 | 11/1963 | Weisenborn et al. | 260/586 E |
| 3,920,703 | 11/1975 | Alig et al. | 260/586 E |
| 3,984,476 | 10/1976 | Fürst et al. | 260/586 E |

FOREIGN PATENT DOCUMENTS 1493183  6/1969  Fed. Rep. of Germany ....... 260/586 E

*Primary Examiner*—Gerald A. Schwartz
*Attorney, Agent, or Firm*—Jon S. Saxe; George M. Gould

[57] ABSTRACT

The present disclosure relates to novel D-homosteroids. More particularly, the invention is concerned with hormonally active novel D-homosteroids, a process for the manufacture thereof and pharmaceutical preparations containing same.

32 Claims, No Drawings

NOVEL D-HOMOSTEROIDS

This is a continuation, of application Ser. No. 736,282 filed Oct. 28, 1976, now abandoned.

DESCRIPTION OF THE INVENTION

The novel D-homosteroids provided by the present invention have the following general formula

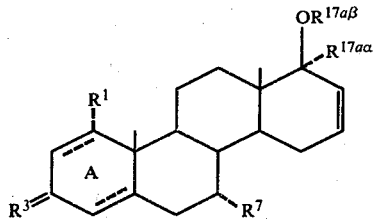

wherein the broken lines in the A-ring denote optional carbon-carbon bonds; $R^1$ represents a hydrogen atom or a methyl group; $R^3$ represents an oxo group or, when the A-ring is unsaturated, an oxo, (α—H, β—OH) or (α—H, β—O-actyl) group; $R^7$ represents a hydrogen atom or a methyl group; $R^{17a\beta}$ represents a hydrogen atom or a $C_1$–$C_{10}$ alkyl, benzyl, cyclohexylmethyl, acyl, tetrahydropyranyl or cycloalkenyl group; and $R^{17a\alpha}$ represents a hydrogen atom or a lower alkyl, ethynyl, vinyl or propadienyl group.

As used in this specification, the term "acyl" denotes, in particular, acyl groups derived from organic acids; for example, from alkanecarboxylic acids containing up to 11 carbon atoms (especially from lower alkanecarboxylic acids containing up to 7 carbon atoms) such as acetic acid, propionic acid, caproic acid, valeric acid, oenanthic acid or undecylenic acid; or from oxalic acid, succinic acid or citric acid, or from aromatic carboxylic acids such as benzoic acid, phenylacetic acid or phenoxyacetic acid, or from heterocyclic carboxylic acids such as nicotinic acid, or from cycloaliphatic carboxylic acids such as cyclopentylpropionic acid.

Lower alkyl groups can contain up to 7 carbon atoms and can be straight-chain or branched-chain. Examples of such lower alkyl groups are methyl, ethyl, propyl, isopropyl, butyl and isomers of the latter. The preferred lower alkyl groups are methyl and ethyl. An alkyl group denoted by $R^{17a\beta}$ can contain up to 10 carbon atoms. Examples of such alkyl groups are methyl, ethyl, propyl, butyl, pentyl, hexyl, heptyl and decyl.

Cycloalkenyl groups preferably contain from 5 to 8 carbon atoms. Examples of such groups are cyclopenten-1-yl and cyclohexen-1-yl.

A preferred group of D-homosteroids of formula I comprises those in which $R^1$ represents a hydrogen atom, $R^3$ represents an oxo group and the A-ring contains a double-bond. In addition, those D-homosteroids of formula I in which $R^{17a\alpha}$ represents a hydrogen atom or a methyl or ethyl group and $R^{17a\beta}$ represents a hydrogen atom or a lower alkanoyl group are preferred. Examples of D-homosteroids of formula I are:

17aβ-(3-Cyclopentyl)propionoxy-D-homoandrosta-4,16-dien-3-one,
17aβ-nicotinyloxy-D-homoandrosta-4,16-dien-3-one,
17aβ-propionoxy-D-homoandrosta-1,4,16-trien-3-one,
17aβ-hydroxy-7α-methyl-D-homoandrosta-1,4,16-trien-3-one,
1α,7α-dimethyl-17aβ-hydroxy-D-homoandrosta-4,16-dien-3-one,
17aβ-hydroxy-7α-methyl-D-homoandrosta-4,16-dien-3-one,
17aβ-hydroxy-7α-methyl-D-homo-5α-androst-16-en-3-one,
17aβ-hydroxy-7α-methyl-D-homo-5α-androsta-1,16-dien-3-one,
17aβ-hydroxy-1-methyl-D-homo-5α-androsta-1,16-dien-3-one,
1α,17aα-dimethyl-D-homoandrosta-4,16-dien-3-one,
3β,17aβ-dihydroxy-17aα-methyl-D-homo-5α-androsta-1,16-diene,
17aβ-hydroxy-17aα-methyl-D-homo-5α-androsta-1,16-dien-3-one,
17aβ-hydroxy-1α,17aα-methyl-D-homo-5α-androst-16-en-3-one,
17aβ-hydroxy-17aα-ethyl-D-homo-5α-androst-16-en-3-one,
17aα-ethyl-17aβ-hydroxy-1α-methyl-D-homo-5α-androst-16-en-3-one,
17aβ-hydroxy-1α-methyl-D-homo-5α-androst-16-en-3-one,
17aβ-hydroxy-7α,17aα-dimethyl-D-homoandrosta-4,16-dien-3-one,
17aβ-pentyloxy-D-homoandrosta-4,16-dien-3-one,
17aβ-n-decyloxy-D-homoandrosta-4,16-dien-3-one,
17aβ-benzyloxy-D-homoandrosta-4,16-dien-3-one,
17aβ-cyclohexylmethyl-D-homoandrosta-4,16-dien-3-one and
17aβ-undecanoyloxy-D-homoandrosta-4,16-dien-3-one.

According to the process provided by the present invention, the D-homosteroids of formula I hereinbefore are manufactured by (a) oxidising the 3-hydroxy or 3-hydroxy-Δ⁵ grouping in a D-homosteroid of the general formula

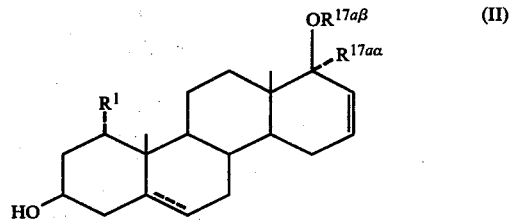

wherein $R^1$, $R^{17a\beta}$ and $R^{17a\alpha}$ have the significance given earlier and the broken line in the 5,6-position denotes an optional carbon-carbon bond,
to the 3-keto or 3-keto-Δ⁴ grouping, or (b) reacting a D-homosteroid of the general formula

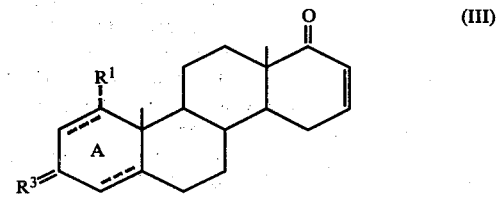

wherein $R^1$, $R^3$ and the broken lines in the A-ring have the significance given earlier,
with an organometallic compound yielding a $R^{17a\alpha}$ group, a 3-keto group being intermediately protected, or (c) reacting a D-homosteroid of the general formula

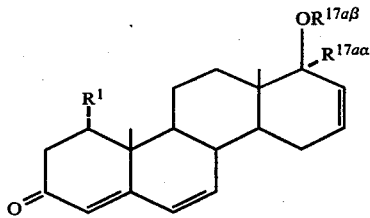

(IV)

wherein $R^1$, $R^{17a\alpha}$ and $R^{17a\beta}$ have the significance given earlier,
with a methyl Grignard compound in the presence of copper-I chloride, or (d) reacting a D-homosteroid of the general formula

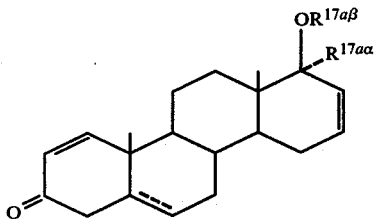

(V)

wherein $R^{17a\alpha}$ and $R^{17a\beta}$ have the significance given earlier and the broken line in the 5,6-position denotes an optional carbon-carbon bond, with a methyl Grignard compound in the presence of copper-I chloride and subsequently rearranging a $\Delta^5$ double bond in the reaction product into the 4,5-position by acid treatment, or (e) acylating the hydroxy group(s) in a D-homosteroid of formula I in which at least one hydroxy group is present in the 3-position or 17aβ-position, or (f) subjecting a D-homosteroid of the general formula

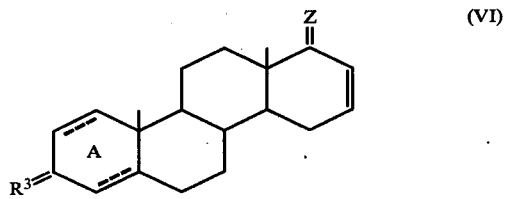

(VI)

wherein $R^3$ and the broken lines in the A-ring have the significance given earlier and Z represents an oxo or $(OR^{17a\beta}, R^{17a\alpha})$ group,
to reduction of the 17a-keto group to the hydroxy group (with intermediate protection of a 3-keto group) when Z represents an oxo group, or to reduction of the 3-keto group and a 17a-keto group which may be present to the hydroxy group when $R^3$ represents an oxo group and the A-ring is monounsaturated, or (g) subjecting a D-homosteroid of formula I which is saturated or monosaturated in the A-ring and in which $R^3$ represents an oxo group to dehydrogenation in the 1,2-position and/or 4,5-position, or (h) converting the 17aβ-hydroxy group in a D-homosteroid of formula I in which $R^{17a\beta}$ represents a hydrogen atom and $R^1$, $R^3$, $R^7$, $R^{17a\alpha}$ and the broken lines in the A-ring have the significance given earlier into a cycloalkenyl, tetrahydropyranyl, $C_1$-$C_{10}$ alkyl, benzyl or cyclohexylmethyl ether, or (i) subjecting a D-homosteroid of formula I in which $R^{17a\beta}$ represents an acyl, tetrahydropyranyl or cycloalkenyl group and $R^1$, $R^3$, $R^7$, $R^{17a\alpha}$ and the broken lines in the A-ring have the significance given earlier to saponification of a 17aβ-acyloxy group and a 3-acyloxy group which may be present or to cleavage of a 17aβ-tetrahydropyranyl or cycloalkenyl ether, or (j) hydrogenating the ethynyl group in a D-homosteroid of the general formula

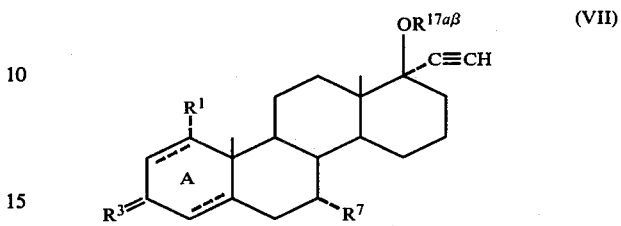

(VII)

wherein $R^1$, $R^3$, $R^7$, $R^{17a\beta}$ and the broken lines in the A-ring have the significance given earlier, to the vinyl group.

The oxidation according to process embodiment (a) can be carried out in a manner which is known per se according to the Oppenauer procedure (e.g. using aluminium isopropylate or tert.butylate) or by means of oxidising agents such as chromium trioxide (e.g. Jones' reagent) or according to the Pfitzner-Moffatt procedure using dimethylsulphoxide/dicyclohexylcarbodiimide (the initially obtained $\Delta^5$-3-ketone requiring subsequent isomerisation to the $\Delta^4$-3-ketone) or by means of dimethylsulphoxide/pyridine/sulphur trioxide.

The reaction of a D-homosteroid of formula III with an organometallic compound according to process embodiment (b) can also be carried out in a manner which is known per se. The organometallic compound can be a Grignard compound (e.g. ethynylmagnesium bromide, methylmagnesium bromide or vinylmagnesium bromide) or an alkali metal organic compound such as sodium, potassium or lithium acetylide or vinyl lithium. A 3-keto group which is simultaneously present can be intermediately protected, for example as a ketal, enol ether, enamine or semicarbazone.

The 7-methylation of a D-homosteroid of formula IV and the 1-methylation of a D-homosteroid of formula V according to process embodiments (c) and (d) can also be carried out in a manner known per se by reaction with a methyl Grignard compound. In embodiment (d) a 1α-methyl-$\Delta^5$ compound is initially obtained, the $\Delta^5$ double bond of which can be rearranged into the 4,5-position by treatment with ethanolic sulphuric acid whilst warming.

The acylation of a free hydroxy group in the 3-position or 17aβ-position in a D-homosteroid of formula I can be carried out by treatment with a reactive acid derivative (e.g. an acid halide or acid anhydride) in the presence of a base (e.g. pyridine or collidine).

The reduction of a 3-keto or 17a-keto group according to process embodiment (f) can be carried out in a manner known per se using a complex metal hydride; for example, a di(lower alkoxy)aluminium hydride such as diisobutoxyaluminium hydride, a tri(lower alkoxy)aluminium such as triisopropoxyaluminium, lithium aluminium hydride, sodium aluminium hydride, sodium borohydride, trimethoxylithium aluminium hydride or tributoxylithium aluminium hydride. Suitable solvents for this reduction are hydrocarbons (e.g. cyclohexane, benzene or toluene) or ethers (e.g. diethyl ether or tetrahydrofuran). Where a 17a-keto group is to be reduced alone in the presence of a 3-keto group, the 3-keto group is intermediately protected. A 3-keto group can be protected in the presence of a 4,5-double bond in the form of an enamine or enol ether. A non-conjugated 3-keto group can be protected as a ketal. The introduction and splitting off of these protecting groups can be carried out according to known procedures.

A 1,2-dehydrogenation according to process embodiment (g) can be carried out in a manner known per se using a dehydrogenating agent such as selenium dioxide, 2,3-dichloro-5,6-dicyanobenzoquinone, thallium triacetate or lead tetraacetate. The 1,2-dehydrogenation can also be carried out microbiologically; for example, using Schizomycetes, in particular those of the genus Arthrobacter (e.g. *A. simplex* ATCC 6946), Bacillus (e.g. *B. lentus* ATCC 13805 and *B. sphaericus* ATCC 7055), Pseudomonas (e.g. *P. aeruginosa* IFO 3505), Flavobacterium (e.g. flavenscens IFO 3058), Lactobacillus (e.g. *L. brevis* IFO 3345) and Nocardia (e.g. *N. opaca* ATCC 4276).

Double bonds can be simultaneously in the 1,2- and 4,5-positions by bromination to give a 2,4-dibromo-3-ketone and dehydrobromination of the latter using lithium carbonate and lithium bromide in dimethylformamide. A 4,5-double bond can also be introduced by brominating a 3-keto-steroid, which is saturated in the A-ring, in glacial acetic acid to give a 2α,4α-dibromo derivative, reducing said derivative with chromium-II chloride to give a 4α-bromo compound and then dehydrobrominating said 4α-bromo compound, via the semicarbazone, by treatment with succinic acid to give a $\Delta^4$-3-ketone.

The etherification of a 17aβ-hydroxy group according to process embodiment (h) can be carried out, for example, by treatment with dihydropyran in order to manufacture a tetrahydropyranyl ether or by treatment with a cycloalkanone ketal in the presence of a catalytic amount of acid (e.g. p-toluenesulphonic acid) in order to manufacture a cycloalkenyl ether. For the manufacture of a 17aβ-$C_1$–$C_{10}$ alkyl, benzyl or cyclohexylmethyl ether, it is expedient to intermediately protect a 3-keto group. The protection of a 3-keto group is preferably accomplished by ketalisation (e.g. with ethyleneglycol in the presence of a catalytic amount of acid such as p-toluenesulphonic acid). The etherification of the 17aβ-hydroxy group can be carried out by conversion into an alkali metal salt (e.g. the sodium salt) with a strong base (e.g. sodium hydride) followed by reaction with a $C_1$–$C_{10}$ alkyl, benzyl or cyclohexylmethyl halide such as pentyl iodide, benzyl chloride or cyclohexylmethyl iodide in a solvent such as dimethylsulphoxide or benzene.

The saponification of 17aβ-acyloxy and 3-acyloxy groups or the cleavage of 17aβ-ether groups according to process embodiment (i) can be carried out in a manner known per se. Acyloxy groups can be saponified, for example, with aqueous-alcoholic bases such as aqueous-methanolic potassium carbonate and ether groups can be cleaved by means of aqueous-alcoholic mineral acids or organic acids such as oxalic acid or p-toluenesulphonic acid.

The hydrogenation of the ethynyl group according to process embodiment (j) can be carried out in the presence of a noble-metal catalyst such as palladium/calcium carbonate and, conveniently, a deactivator such as pyridine.

The starting materials used in the foregoing process, insofar as they are not known or insofar as their preparation is not described hereinafter, can be prepared in analogy to known methods or methods described in the Examples hereinafter.

The D-homosteroids of formula I possess hormonal activity. D-Homosteroids of formula I in which $R^{17a\alpha}$ represents a hydrogen atom or a lower alkyl group possess, in particular, androgenic/anabolic activity. D-Homosteroids of formula I in which $R^{17a\alpha}$ represents an ethynyl, vinyl or propadienyl group possess, in particular, gestation-inhibiting and ovulation-inhibiting activity.

For example, 17aβ-hydroxy-D-homoandrosta-4,16-dien-3-one shows, on subcutaneous administration to juvenile male rats, an androgenic activity which is comparable with the action of testosterone at one third of the dosage. The androgenic activity was determined on the basis of the growth of the prostate gland and the seminal vesicle. 17aβ-Phenylacetoxy- and 17aβ-phenoxyacetoxy-D-homoandrosta-4,16-dien-3-one showed, on subcutaneous administration to juvenile male rats, an extended period of activity compared with testosterone enanthate.

The D-homosteroids of formula I can be used as medicaments; for example in the form of pharmaceutical preparations which contain them in association with a compatible pharmaceutical carrier material. This carrier material can be an organic or inorganic inert carrier material which is suitable for enteral, percutaneous or parenteral administration such as, for example, water, gelatin, gum arabic, lactose, starch, magnesium stearate, talc, vegetable oils, polyalkylene glycols, petroleum jelly etc. The pharmaceutical preparations can be made up in a solid form (e.g. as tablets, dragées, suppositories or capsules) or in a liquid form (e.g. as solutions, suspensions or emulsions). If necessary, the pharmaceutical preparations may be sterilised and/or may contain adjuvants such as preservatives, stabilisers, wetting agents or emulsifiers, salts for modifying the osmotic pressure or buffers. They may also contain other therapeutically valuable substances.

The following Examples illustrate the process provided by the present invention:

EXAMPLE 1

50.0 g of 3β-hydroxy-D-homoandrosta-5,16-dien-17a-one were dissolved in 1000 ml of cyclohexanone and 3000 ml of toluene. 400 ml of solvent were evaporated off from this solution and the solution was cooled to 80° C. and treated with 60.0 g of aluminum tert.butylate. Whilst stirring and flushing with argon, the mixture was heated to reflux for 2.5 hours under a water separator. For the working-up, the solution was concentrated in vacuo to about 200 ml, poured on to an ice-cold mixture of 1500 ml of water and 50 ml of concentrated hydrochloric acid and extracted with methylene chloride. The organic extract was washed with water, dried over sodium sulphate, evaporated in vacuo and finally dried at 50° C. under a high vacuum. The residue was then recrystallised from acetone/hexane. There were obtained 40.7 g of pure D-homoandrosta-4,16-diene-3,17a-dione of melting point 193°–194° C.; UV: $\epsilon_{236}$=21500; $[\alpha]_D^{25°}$ C.=+60° (c=0.1 in dioxan).

The starting material was prepared as follows:

18.1 g of 3β-acetoxy-D-homoandrost-5-ene-17a-one were dissolved in 800 ml of methanol under argon at 45° C. 23.5 g of copper-II bromide were added to this solution and the mixture was heated under reflux for 18 hours. The mixture was cooled to 35° C. and filtered and the residue was then rinsed thoroughly with chloroform. The combined filtrates were poured on to 1.3 liters of water containing 100 g of sodium chloride and 500 g of ice. The mixture was extracted three times with chloroform. The organic phases were washed with sodium chloride solution, dried over magnesium sulphate and evaporated in vacuo. There were obtained 19.8 g of almost pure 17α-bromo-3β-hydroxy-D-homoandrost-5-en-17a-one, which was used directly in the next step.

35.1 g of calcium carbonate were suspended in 290 g of dimethylacetamide. Whilst flushing with argon, 40 ml of dimethylacetamide were distilled off and then 18.7 g of 17α-bromo-3β-hydroxy-D-homoandrost-5-en-17a-one were added over a period of 20 minutes. The mixture obtained was then boiled under reflux for 30 minutes. The solution was cooled to 60° C. and the precipitate filtered off. The filtrate was poured on to a mixture of 1.25 liters of water, 450 g of ice and 170 g of sodium chloride. The mixture was extracted three times with methylene chloride. The extracts were washed with 1-N hydrochloric acid and water, dried over magnesium sulphate and evaporated in vacuo. There were obtained 14.7 g of crude product which was dissolved in 170 ml of ethyl acetate and treated with a small amount of active charcoal. After filtering the solution over Speedex Dicalite, the filtrate was concentrated to 50 ml and left to crystallise. There were thus obtained 11.7 g of pure 3β-hydroxy-D-homoandrosta-5,16-dien-17a-one of melting point 190°–193° C.; UV: $\epsilon_{227}=13000$; $[\alpha]_D^{25°}$ C.$=-177°$ (c=0.1 in dioxan).

EXAMPLE 2

15.0 g of D-homoandrosta-4,16-dien-3,17a-dione were dissolved in 150 ml of methanol and boiled under reflux for 10 minutes with 8.1 ml of pyrrolidine with the exclusion of air. The solution was cooled to $-10°$ C. The enamine which had crystallised out was filtered off and dried at 20° C. under a high vacuum. There were obtained 16.1 g of pure 3-(1-pyrrolidinyl)-D-homoandrosta-3,5,16-trien-17a-one of melting point 207°–210° C.; UV: $\epsilon_{279}=19500$; $\epsilon_{227}=13000$; $[\alpha]_D^{25°}$ C.$=-295°$.

16.1 g of the foregoing enamine were dissolved in 750 ml of absolute tetrahydrofuran and added dropwise over a period of 15 minutes to a well-stirred solution of 8.0 g of lithium aluminium hydride in 750 ml of absolute ether at 0° C. The mixture was then stirred for a further 1 hour at 0° C. For the working-up, the solution was initially cautiously treated with 300 ml of moist ether. 40 ml of saturated sodium sulphate solution were then added, the mixture was stirred for a further 10 minutes and the precipitate was filtered off. The filtrate was evaporated in vacuo. There were obtained 15.8 g of substance which was warmed to 50° C. with a mixture of 1000 ml of methanol and 200 ml of 2-N sodium hydroxide solution for 45 minutes while stirring and flushing with argon. The solution was then poured on to 6 liters of ice-water and 200 ml of acetic acid and extracted three times with methylene chloride. The organic extract was washed with water, dried over sodium sulphate and evaporated in vacuo. The residue was chromatographed on 650 g of silica gel. Elution with acetone/hexane (1:1) yielded 13.0 g of pure 17aβ-hydroxy-D-homoandrosta-4,16-dien-3-one of melting point 183°–185° C.; UV: $\epsilon_{241}=16200$; $[\alpha]_D^{25°}$ C.$=+76°$.

EXAMPLE 3

A solution of 6.3 g of 17aβ-hydroxy-D-homoandrosta-4,16-dien-3-one in 60 ml of pyridine and 60 ml of acetic anhydride was maintained at room temperature overnight. The solvent was then removed in vacuo and the residue was recrystallized from acetone/hexane. There were obtained 6.0 g of pure 17aβ-acetoxy-D-homoandrosta-4,16-dien-3-one of melting point 165°–167° C.; UV: $\epsilon_{240}=17000$; $[\alpha]_D^{25°}$ C.$=+91°$ (c=0.1 in dioxan).

The following D-homosteroids were prepared in an analogous manner using the corresponding acid anhydride:

17aβ-Propionoxy-D-homoandrosta-4,16-dien-3-one of melting point 139°–140° C. and
17aβ-butyroxy-D-homoandrosta-4,16-dien-3-one of melting point 117°–118° C.

EXAMPLE 4

2.0 ml of phenylacetyl chloride were added dropwise to a solution of 2.0 g of 17aβ-hydroxy-D-homoandrosta-4,16-dien-3-one in 20 ml of pyridine over a period of 15 minutes and the mixture was warmed to 60° C. for 5 hours. For the working-up, the mixture was poured on to water and extracted with methylene chloride. The organic extract was washed neutral with dilute hydrochloric acid, sodium hydrogen carbonate solution and water, dried over sodium sulphate and evaporated in vacuo. The residue was chromatographed on silica gel. Elution with hexane/acetone (9:1) yielded 1.7 g of pure 17aβ-phenylacetoxy-D-homoandrosta-4,16-dien-3-one of melting point 135°–136° C. (from acetone/hexane); UV: $\epsilon_{240}=17200$; $[\alpha]_D^{25°}$ C.$=+108°$ (c=0.1 in dioxan).

The following D-homosteroids were prepared in an analogous manner using the corresponding chloride:

17aβ-Undecanoyloxy-D-homoandrosta-4,6-dien-3-one; amorphous; $[\alpha]_D^{25°}$ C.$=+80°$ (c=0.1 in dioxan); $\epsilon_{240}=17100$,
17aβ-heptanoyloxy-D-homoandrosta-4,16-dien-3-one; oily; $[\alpha]_D^{25°}$ C.$=+88°$ (c=0.1 in dioxan) and
17aβ-phenoxyacetoxy-D-homoandrosta-4,16-dien-3-one of melting point 174°–176° C.

EXAMPLE 5

1.0 g of 17aβ-hydroxy-D-homoandrosta-4,16-dien-3-one was dissolved in 40 ml of absolute benzene and then 10 ml of benzene were distilled off. A solution of 5 mg of p-toluenesulphonic acid in 10 ml of benzene and 0.6 ml of dihydropyran was added to the remaining solution and the mixture was held for 30 minutes at room temperature. For the working-up, the solution was washed neutral, in sequence, with sodium hydrogen carbonate solution and water, dried over sodium sulphate and evaporated in vacuo. The residue was recrystallised from ether/hexane and gave pure 17aβ-tetrahydropyranyloxy-D-homoandrosta-4,16-dien-3-one of melting point 137°–138° C.; UV: $\epsilon_{240}=16650$; $[\alpha]_D^{25°}$ C.$=+64°$ (c=0.1 in dioxan).

EXAMPLE 6

A solution of 2.0 g of 17aβ-hydroxy-D-homoandrosta-4,16-dien-3-one in 40 ml of cyclopentanone diethyl ketal was warmed to 120° C. for 6 hours. The solution was evaporated to dryness in vacuo and the residue was chromatographed on 40 g of aluminium oxide (activity grade II). By elution with benzene there were obtained 1.2 g of pure 17aβ-cyclopentenyloxy-D-homoandrosta-4,16-dien-3-one of melting point 135°–137° C. (from methanol); $[\alpha]_D^{25°}$ C. = +100° (c=0.1 in dioxan); UV: $\epsilon_{240}$= 17200.

EXAMPLE 7

A solution of 342 mg of 17aβ-acetoxy-D-homoandrosta-4,16-dien-3-one and 328 mg of 2,3-dichloro-5,6-dicyanobenzoquinone (DDQ) in 30 ml of benzene was heated under reflux for 24 hours. The solution was cooled and filtered over a column of 10 g of aluminium oxide (activity grade II). The column was then completely eluted with 200 ml of ethyl acetate. The combined eluates yielded 270 mg of crystalline material which, upon recrystallisation from acetone/hexane, yielded pure 17aβ-acetoxy-D-homoandrosta-1,4,16-trien-3-one of melting point 222°-224° C.; UV: $\epsilon_{244}$=14800; $[\alpha]_D^{25°}$ C. = +53°.

17aβ-Hydroxy-17aα-methyl-D-homoandrosta-1,4,16-trien-3-one was prepared in an analogous manner from 17aβ-hydroxy-17a-methyl-D-homoandrosta-4,16-dien-3-one. Melting point 148°-150° C.; UV: $\epsilon_{245}$=15500; $[\alpha]_D^{25°}$ C. = −34°.

EXAMPLE 8

1.95 g of a 50% dispersion of sodium hydride in oil were dissolved in 45 ml of tetrahydrofuran and 10 ml of dimethyl sulphoxide. The solution was stirred at room temperature for 30 minutes and then 1.3 g of 3,3-ethylenedioxy-17aβ-hydroxy-D-homoandrosta-4,16-diene were added. The mixture was stirred for a further 30 minutes and then 3.9 ml of 1-iodo-pentane were added. Subsequently, the mixture was stirred at room temperature for 20 hours. For the working-up, the mixture was treated cautiously with water and extracted with methylene chloride. The organic extracts were washed with water, dried over sodium sulphate and evaporated in a vacuum. The residue was dissolved in 65 ml of acetone, treated with 6.5 ml of water and 1.3 g of p-toluenesulphonic acid and stirred at room temperature for 2.5 hours. The mixture was poured on to water, extracted with methylene chloride, dried over sodium sulphate and evaporated. The residue was chromatographed on 110 g of silica gel. Elution with hexane/acetone (8:1) yielded 0.3 g of pure 17aβ-pentyloxy-D-homoandrosta-4,16-dien-3-one of melting point 58°-59° C. (from methanol/water); $[\alpha]_D^{25°}$ C. = +112° (c=0.1 in dioxan); $\epsilon_{240}$=16700.

The starting material was prepared as follows:

3.4 g of 17aβ-acetoxy-D-homoandrosta-4,16-dien-3-one, 100 ml of ethylene glycol, 100 ml of methylene chloride, 15 ml of ethyl orthoformate and 150 mg of p-toluenesulphonic acid were warmed to 40° C. for 75 minutes. Usual working-up yielded 5.2 g of 3,3-ethylenedioxy-17aβ-acetoxy-D-homoandrosta-4,16-diene which was saponified with 300 ml of 5% methanolic potassium hydroxide in 100 ml of methylene chloride at room temperature to give 3,3-ethylenedioxy-17aβ-hydroxy-D-homoandrosta-4,16-diene of melting point 168°-173° C.

The following D-homosteroids were prepared in a manner analogous to that described in the first paragraph of this Example:

17aβ-n-Decyloxy-D-homoandrosta-4,16-dien-3-one;
  oily; $[\alpha]_D^{25°}$ C. = +94° (c=0.1 in dioxan); $\epsilon_{240}$=16650,
17aβ-benzyloxy-D-homondrosta-4,16-dien-3-one of melting point 139°-141° C. (from acetone/hexane); $[\alpha]_D^{25°}$ C. = +130°; $\epsilon_{240}$=16600 and 17aβ-cyclohexylmethyl-D-homoandrosta-4,16-dien-3-one of melting point 98°-99° C.; $[\alpha]_D^{25°}$ C. = +112°; $\epsilon_{241}$=16700.

EXAMPLE 9

A solution of 6.0 g of D-homoandrosta-4,16-dien-3,17a-dione in 100 ml of tetrahydrofuran and 100 ml of ether was added dropwise to a solution of 3.0 g of lithium aluminium hydride in 400 ml of absolute ether while stirring and cooling to 0° C. and the mixture was then stirred for a further 1 hour at 0°-5° C. For the working-up, the mixture was cautiously treated with 300 ml of moist ether and then with 10 ml of saturated sodium sulphate solution. The mixture was stirred for a further 15 minutes and then the precipitate was filtered off and rinsed thoroughly with methylene chloride. The combined filtrates were evaporated in vacuo. The residue was chromatographed on 330 g of silica gel and yielded 4.1 g of pure 3β,17aβ-dihydroxy-D-homoandrosta-4,16-diene of melting point 158°-162° C. (from acetone/hexane); $[\alpha]_D^{25°}$ C. = +23° (c=0.1 in dioxan).

A solution of 3.0 g of 3β,17aβ-dihydroxy-D-homoandrosta-4,16-diene in 50 ml of pyridine and 50 ml of acetic anhydride was maintained at room temperature for 18 hours. The solution was then evaporated in vacuo and the residue was recrystallised from methanol. There was obtained pure 3β,17aβ-diacetoxy-D-homoandrosta-4,16-diene of melting point 115°-116° C; $[\beta]_D^{25°}$ C. = +12°.

EXAMPLE 10

A solution of 7.0 g of 3,3-dimethoxy-D-homo-5β-androst-16-en-17a-one in 280 ml of ether was added dropwise to a stirred solution, cooled to 0° C., of 3.5 g of lithium aluminium hydride in 420 ml of ether. The mixture was stirred for 1 hour at 0°-5° C. and then cautiously treated with 250 ml of water-saturated ether. The mixture was stirred for a further 15 minutes at room temperature and the pure precipitate was then filtered off. This precipitate was thoroughly extracted with methylene chloride. The filtrate was evaporated in vacuo. There were obtained 7.0 g of crude product which was dissolved in 140 ml of acetone and treated with a solution of 2.1 g of p-toluenesulphonic acid in 14 ml of water. The solution was maintained at room temperature for 2 hours and then treated with 500 ml of water. The precipitate which separated out was filtered off. For purification, this precipitate was chromatographed on a 50-fold amount of silica gel. Following elution with methylene chloride/acetone (95:5) there were obtained 5.0 g of pure 17aβ-hydroxy-D-homo-5α-androst-16-en-3-one of melting point 203°-205° C. (from acetone/hexane); $[\alpha]_D^{25°}$ C. = +1° (c=0.1 in dioxan).

The starting material was prepared as follows:

3β-Acetoxy-D-homoandrost-5-en-17a-one was reduced in ethanol using palladium/carbon as the catalyst to give 3β-acetoxy-D-homo-5α-androstan-17a-one of melting point 113°-115° C. This was brominated with copper bromide in methanol and converted into 3β-hydroxy-D-homo-androst-16-en-17a-one of melting point 177°-179° C. by treatment with calcium carbonate in dimethylacetamide. Oxidation of the latter compound with Jones' reagent gave D-homo-5α-androst-16-ene-3,17a-dione of melting point 200°-202° C. ($\epsilon_{223}$=8700). Reaction of this latter compound with methanol and catalytic amounts of p-toluenesulphonic acid at the reflux temperature finally gave 3,3-dimethoxy-D-homo-5α-androst-16-en-17a-one of melting point 125°–127° C. (from ether/hexane); $[\alpha]_D^{25°}$ C.=−33°; $\epsilon_{223}$=8650.

EXAMPLE 11

A solution of 3.0 g of 3,3-dimethoxy-D-homo-5α-androst-16-en-17a-one in 20 ml of tetrahydrofuran and 20 ml of ether was added to 70 ml of a 2-M solution of methyl lithium in ether over a period of 30 minutes while stirring. The solution was stirred overnight at room temperature and then worked-up in the customary manner. There were obtained 3.2 g of crude product which was dissolved in 50 ml of acetone and treated with a solution of 1.0 g of p-toluenesulphonic acid in 5 ml of water. The mixture was maintained at room temperature for 2 hours, treated with water and extracted with methylene chloride. After chromatography on silica gel, the residue gave pure 17aβ-hydroxy-17aα-methyl-D-homo-5α-androst-16-en-3-one of melting point 211°–214° C.; $[\alpha]_D^{25°}$ C.=−52° (c=0.1 in dioxan).

EXAMPLE 12

2.0 g of 17aβ-hydroxy-D-homo-5α-androst-16-en-3-one were acetylated at room temperature with 50 ml of pyridine and 50 ml of acetic anhydride. The 17a-acetate obtained by customary working-up was dissolved in 20 ml of dioxan and, after the addition of 3 drops of 40% hydrogen bromide/glacial acetic acid solution over a period of 30 minutes, treated with a solution of 0.36 ml of bromine and 570 mg of sodium acetate in 37 ml of glacial acetic acid. The mixture was then poured on to ice-water. The crystals which precipitated out were filtered off under suction, washed with water and dried over potassium hydroxide in vacuo. There were obtained 3.1 g of product which was dissolved in 20 ml of dimethylacetamide and added over a period of 20 minutes to a boiling mixture of 5.1 g of calcium carbonate and 45 ml of dimethylacetamide. The mixture was subsequently boiled under reflux for a further 30 minutes, then cooled to 60° C. and the calcium salts were filtered off. The filtrate was diluted with water and extracted with methylene chloride. The organic extracts were washed with water, dried over sodium sulphate and evaporated in vacuo. There were obtained 2.2 g of crude product which was chromatographed on a 50-fold amount of silica gel. Elution with methylene chloride yielded 1.2 g of pure 17aβ-acetoxy-D-homoandrosta-1,6-dien-3-one of melting point 133°–135° C.; $[\alpha]_D^{25°}$ C.=+55°; UV: $\epsilon_{229}$=11100.

EXAMPLE 13

A solution of 2.5 g of 3β-acetoxy-D-homoandrosta-5,16-dien-17a-one in 15 ml of tetrahydrofuran and 15 ml of ether was added dropwise to 60 ml of a 1.2-M solution of lithium methyl in ether while stirring and flushing with argon over a period of 30 minutes. The mixture was stirred overnight at room temperature, then poured on to ice-water and extracted with ether. The ether extracts were washed with water, dried over sodium sulphate and evaporated in vacuo. After a two-fold recrystallisation from acetone, there was obtained pure 3β,17aβ-dihydroxy-17aα-methyl-D-homoandrosta-5,16-diene of melting point 220°–223° C; $[\alpha]_D^{25°}$ C.==169° (c=0.1 in dioxan).

10 ml of toluene were distilled off from a solution of 1.5 g of 3β,17aβ-dihydroxy-17a-methyl-D-homoandrosta-5,16-diene in 20 ml of cyclohexanone and 55 ml of toluene. The mixture was then cooled to 100° C. and 1.73 g of aluminium tert.butylate were added. The mixture was then boiled under reflux for 2 hours under a water separator. Customary working-up (see Example 1) yielded 2.7 g of crude product which was chromatographed on silica gel. There were obtained 1.2 g of pure 17aβ-hydroxy-17aα-methyl-D-homo-androsta-4,16-dien-3-one of melting point 152°–154° C. (from acetone/hexane); UV: $\epsilon_{241}$=16700; $[\alpha]_D^{25°}$ C.=+18° (c=0.1 in dioxan).

EXAMPLE 14

A solution of 2.0 g of 17aβ-hydroxy-17aα-methyl-D-homoandrosta-4,16-dien-3-one in 100 ml of absolute tetrahydrofuran and 100 ml of abosolute ether was added dropwise to a solution, cooled to 0° C., of 1.0 g of lithium aluminium hydride in 200 ml of ether. After completion of the addition, the mixture was stirred for a further 1 hour at 0° C. and then worked-up in the customary manner (see Example 2). By recrystallisation of the crude product from acetone/hexane there was obtained pure 3β,17aβ-dihydroxy-17aα-methyl-D-homoandrosta-4,16-diene of melting point 137°–141° C.; $[\alpha]_D^{25°}$ C.=−28° (c=0.1 in dioxan).

EXAMPLE 15

Acetylene was passed into a solution of 2.0 g of potassium in 100 ml of liquid ammonia until the solution became decolorised. A solution of 3.4 g of 3β-actoxy-D-homoandrosta-5,16-dien-17a-one in 70 ml of tetrahydrofuran was then added dropwise over a period of 1 hour, a weak stream of acetylene still being passed through the solution. For the working-up, 30 ml of ammonium chloride solution were slowly added dropwise and the ammonia was allowed to evaporate overnight. The mixture was treated with water and extracted with ether/methylene chloride. The organic extracts were washed with water, dried over sodium sulphate and evaporated in vacuo. The residue was chromatographed on silica gel. Elution with hexane/acetone (5:1) yielded pure 17aα-ethynyl-3β,17aβ-dihydroxy-D-homoandrosta-5,16-diene of melting point 227°–229° C. (from acetone/isopropyl ether); $[\alpha]_D^{25°}$ C.=−307° (c=0.1 in dioxan).

1.1 g of 17aα-ethynyl-3β,17aβ-dihydroxy-D-homoandrosta-5,16-diene were dissolved in 15 ml of cyclohexanone and 40 ml of toluene. After the distillation of 8 ml of solvent, 1.27 g of aluminium tert.butylate were added and the mixture was heated at reflux for 2 hours under a water separator. The mixture was worked-up in the customary manner and gave 1.5 g of crude product which, after chromatography on silica gel, yielded pure 17aα-ethynyl-17aβ-hydroxy-D-homoandrosta-4,16-dien-3-one of melting point 247°–250° C.; UV: $\epsilon_{239}$=16800; $[\alpha]_D^{25°}$ C.=−138° (c=0.1 in dioxan).

EXAMPLE 16

649 mg of 17aα-ethynyl-17aβ-hydroxy-D-homoandrosta-4,16-dien-3-one were dissolved in 40 ml of ethyl acetate and 5 ml of pyridine and, after the addition of 300 mg of palladium/calcium carbonate, the mixture was hydrogenated under normal pressure until 1.1 equivalents of hydrogen had been absorbed. The catalyst was filtered off and the solvent evaporated in vacuo. The residue was recrystallised from acetone/hexane. There was thus obtained pure 17aβ-hydroxy-17aα-vinyl-D-homoandrosta-4,16-dien-3-one of melting

EXAMPLE 17

A solution of 16 g of pyridine/sulphur trioxide complex in 64 ml of dimethylsulphoxide was added dropwise to 8 g of 3ξ-hydroxy-1α-methyl-17aβ-tetrahydropyranyloxy-D-homo-5α-androst-16-ene in 230 ml of dimethylsulphoxide and 21.2 ml of triethylamine at 15° C. over a period of 45 minutes and the mixture was subsequently stirred for 1 hour at room temperature. The mixture was poued on to ice-water and the precipitate filtered off, washed and taken up in ether. After drying and evaporation, 7.5 g of 1α-methyl-17aβ-tetrahydropyranyloxy-D-homo-5α-androst-16-en-3-one were obtained.

The starting material was prepared as follows:

50 g of 17β-hydroxy-1α-methyl-5α-androstan-3-one were heated at reflux in 1000 ml of absolute benzene, 125 ml of ethylenegycol and 1.25 g of p-toluenesulphonic acid for 7 hours while stirring under a water separator. The solution was then diluted with ether, washed with sodium hydrogen carbonate solution and water, dried and evaporated to dryness. 55 g of 3,3-ethylenedioxy-17β-hydroxy-1α-methyl-5α-androstane were obtained.

55 g of 3,3-ethylenedioxy-17β-hydroxy-1α-methyl-5α-androstane in 550 ml of toluene and 110 ml of cyclohexanone were treated at boiling with a solution of 5.5 g of aluminium isopropylate in 55 ml of toluene and the mixture was heated for 3 hours with slow distillation. The mixture was then treated with ether, washed with ice-cold dilute sulphuric acid and water, evaporated and the residue steam-distilled. After extraction with methylene chloride, the resulting product was recrystallised from diisopropyl ether to give 51 g of 3,3-ethylenedioxy-1α-methyl-5α-androstan-17-one of melting point 155.5°–156.6° C.

51 g of 3,3-ethylenedioxy-1α-methyl-5α-androstan-17-one in 1000 ml of dimethylformamide were treated with 51 g of trimethylsulphonium iodide and 27.2 g of potassium tert.butylate were introduced portionwise over a period of 30 minutes while stirring. After a further 60 minutes, the mixture was stirred into ice-water and the precipitate which had separated out was filtered off, washed thoroughly with water and taken up in methylene chloride. After evaporation, the residue was chromatographed on silica gel. 36.6 g of 3,3-ethylenedioxy-1α-methyl-5α-androstan[17(β-1′)-spiro-3′]oxirane were thus obtained. A sample recrystallised from diisopropyl ether melted at 165.5°–166.5° C.

36.6 g of 3,3-ethylenedioxy-1α-methyl-5α-androstan-[17(β-1′)-spiro-3′]oxirane in 366 ml of dimethylformamide and 145 ml of water were treated with 41.3 g of sodium azide and the mixture was stirred for 3 hours at 110° C. The mixture was then stirred into ice-water and the precipitate which had separated out was filtered off, washed with water and taken up in methylene chloride. After evaporation, 38 g of 3,3-ethylenedioxy-17α-azidomethyl-17β-hydroxy-1α-methyl-5α-androstane were obtained.

38 g of 3,3-ethylenedioxy-17α-azidomethyl-17β-hydroxy-1α-methyl-5α-androstane in 380 ml of methanol and 38 ml of water were treated with 19 g of oxalic acid and the mixture was heated at reflux for 30 minutes. The solution was treated with water and extracted with ether. The ether phase was washed with water, dried and evaporated. 29.5 g of 17α-azidomethyl-17β-hydroxy-1α-methyl-5α-androstan-3-one were obtained as the residue.

29 g of lithium alanate were suspended in 350 ml of absolute tetrahydrofuran and a solution of 29 g of 17α-azidomethyl-17β-hydroxy-1α-methyl-5α-androstan-3-one in 350 ml of absolute tetrahydrofuran was added dropwise while cooling with ice and stirring. The mixture was subsequently stirred for 1 hour at room temperature. The suspension was then cooled again in an ice-bath and cautiously treated, in sequence, with 31.7 ml of water, 31.7 ml of 15% sodium hydroxide solution and 94 ml of water. The precipitate was filtered off, rinsed with ether and exhaustively extracted with ether in a Soxhlet apparatus. The suction-filtered filtrate ws then combined with the extraction solution and evaporated to give 27.5 g of 17α-aminomethyl-3ξ,17β-dihydroxy-1α-methyl-5α-androstane.

27 g of 17α-aminomethyl-3ξ,17β-dihydroxy-1α-methyl-5α-androstane were dissolved in 558 ml of acetic acid and 558 ml of water were treated slowly, while cooling with ice, with 48.5 g of sodium nitrate dissolved in 381 ml of water. The mixture was subsequently stirred for 1 hour at room temperature, diluted with water and the precipitate which had separated out was filtered off. After dissolving the product in methylene chloride, the solution was washed with sodium hydrogen carbonate solution and water, dried and evaporated. The residue was chromatographed on silica gel. 17.5 g of 3ξ-hydroxy-1α-methyl-D-homo-5α-androstan-17-one were thus obtained.

16 g of 3ξ-hydroxy-1α-methyl-D-homo-5α-androstan-17a-one were heated at reflux in 320 ml of absolute tetrahydrofuran with 22.5 g of copper-II bromide for 90 minutes while stirring. The copper-I bromide which had separated out was filtered off, the filtrate diluted with ether, washed with ammonium chloride solution an water, dried and evaporated. 19.5 g of 17ξ-bromo-3ξ-hydroxy-1α-methyl-D-homo-5α-androstan-17a-one were obtained.

19.5 g of crude 17ξ-bromo-3ξ-hydroxy-1α-methyl-D-homo-5α-androstan-17a-one were stirred for 18 hours at 90° C. in 195 ml of dimethylformamide with 11.1 g of lithium carbonate and 13 g of lithium bromide. The mixture was then precipitated in ice-water and the precipitate was filtered off, washed with water, taken up in methylene chloride, dried and evaporated. The residue was chromatographed on silica gel and there were obtained 11.5 g of 3ξ-hydroxy-1α-methyl-D-homo-5α-androst-16-en-17a-one; UV; $\epsilon_{223}$=7600.

11 g of 3ξ-hydroxy-1α-methyl-D-homo-5α-androst-16-en-17a-one in 44 ml of pyridine were left to stand for 18 hours at room temperature with 22 ml of acetic anhydride. After precipitation in ice-water, the precipitate was filtered off, thoroughly washed out and dried. There were obtained 11.2 g of 3ξ-acetoxy-1α-methyl-D-homo-5α-androst-16-en-17a-one; UV; $\epsilon_{223}$=7200.

11 g of 3ξ-acetoxy-1α-methyl-D-homo-5α-androst-16-en-17a-one in 110 ml of absolute tetrahydrofuran were treated with 22 g of lithium tri-tert.butoxyalanate while cooling with ice and the mixture was subsequently stirred for 4 hours while cooling with ice. The solution was diluted with ether, washed with dilute sulphuric acid and water, dried and evaporated. The residue was chromatographed on silica gel and 8.5 g of 3ξ-acetoxy-17aβ-hydroxy-1α-methyl-D-homo-5α-androst-16-ene were obtained.

8.5 g of 3ξ-acetoxy-17aβ-hydroxy-1α-methyl-D-homo-5α-androst-16-ene in 85 ml of absolute tetrahydrofuran were stirred for 1 hour at room temprature with 8.5 ml of 2,3-dihydro-b 4H-pyran and 1 drop of phosphorus oxychloride. The mixture was then diluted with ether, washed with saturated sodium hydrogen carbonate solution and water, dried and evaporated. 9.7 g of 3ξ-acetoxy-1α-methyl-17aβ-tetrahydropyranyloxy-D-homo-5α-androst-16-ene were obtained.

9.5 g of 3ξ-acetoxy-1α-methyl-17aβ-tetrahydropyranyloxy-D-homo-5α-androst-16-ene in 95 ml of methanol and 9.5 ml of water were heated at reflux for 1 hour with 4.75 g of potassium carbonate. The mixture was precipitated in ice-water and the precipitate was filtered off, washed and taken up in methylene chloride. After drying and evaporation, 8.1 g of 3ξ-hydroxy-1α-methyl-17aβ-tetrahydropyranyloxy-D-homo-5α-androst-16-ene were obtained.

EXAMPLE 18

7 g of 1α-methyl-17aβ-tetrahydropyranyloxy-D-homo-5α-androst-16-en-3-one in 70 ml of methanol and 7 ml of water were heated at reflux for 30 minutes with 3.5 g of oxalic acid. After precipitation with ice-water, the precipitate was filtered off, washed and taken up in methylene chloride. After drying and evaporation, the residue was chromatographed on silica gel. Upon recrystallisation from diisopropyl ether, 3.2 g of 17aβ-hydroxy-1α-methyl-D-homo-5α-androst-16-en-3-one of melting point 189°–191° C. were obtained.

We claim:
1. A D-homosteroid of the formula

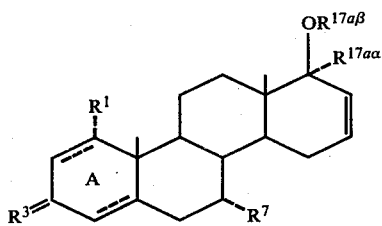

wherein the broken lines in the A-ring denote optional carbon-carbon bonds; $R^1$ is hydrogen or methyl; $R^3$ is oxo or, when the A-ring is unsaturated, oxo, (α—H, β—OH) or (α—H, β—O-acyl) wherein said acyl is derived from a convenional steroid organic carboxylic acid; $R^7$ is hydrogen or methyl; $R^{16a\beta}$ is hydrogen, $C_{1-10}$ alkyl, benzyl, cyclohexylmethyl, acyl, tetrahydropyranyl or cycloalkenyl; and $R^{17a\alpha}$ is hydrogen, lower alkyl, ethynyl, vinyl or propadienyl wherein said acyl is derived from a conventional steroid organic carboxylic acid.

2. A compound of claim 1 wherein there is a double bond in the 4,5-position.

3. The compound of claim 2 which is 17aβ-hydroxy-D-homoandrosta-4,16-dien-3-one.

4. The compound of claim 2 which is 17aβ-acetoxy-D-homoandrosta-4,16-dien-3-one.

5. The compound of claim 2 which is 17aβ-propionoxy-D-homoandrosta-4,16-dien-3-one.

6. The compound of claim 2 which is 17aβ-butyroxy-D-homoandrosta-4,16-dien-3-one.

7. The compound of claim 2 which is 17aβ-phenylacetoxy-D-homo-androsta-4,16-dien-3-one.

8. The compound of claim 2 which is 17aβ-undecanoyloxy-D-homoandrosta-4,16-dien-3-one.

9. The compound of claim 2 which is 17aβ-heptanoyloxy-D-homoandrosta-4,16-dien-3-one.

10. The compound of claim 2 which is 17aβ-phenoxyacetoxy-D-homoandrosta-4,16-dien-3-one.

11. The compound of claim 2 which is 17aβ-tetrahydropyranyloxy-D-homoandrosta-4,16-dien-3-one.

12. The compound of claim 2 which is 17aβ-cyclopentenyloxy-D-homoandrosta-4,16-dien-3-one.

13. The compound of claim 2 which is 3β-17aβ-dihydroxy-D-homoandrosta-4,16-diene.

14. The compound of claim 2 which is 3β,17aβ-diacetoxy-D-homoandrosta-4,16-diene.

15. The compound of claim 2 which is 17aβ,hydroxy-17aα-methyl-D-homoandrosta-4,16-dien-3-one.

16. The compound of claim 2 which is 3β,17aβ-dihydroxy-17aα-methyl-D-homoandrosta-4,16-diene.

17. The compound of claim 2 which is 17aα-ethynyl-3,17aβ-dihydroxy-D-homoandrosta-4,16-dien-3-one.

18. The compound of claim 2 which is 17aβ-pentyloxy-D-homoandrosta-4,16-dien-3-one.

19. The compound of claim 2 which is 17aβ-n-decyloxy-D-homoandrosta-4,16-dien-3-one.

20. The compound of claim 2 which is 17aβ-benzyloxy-D-homoandrosta-4,16-dien-3-one.

21. The compound of claim 2 which is 17aβ-cyclohexylmethyl-D-homoandrosta-4,16-dien-3-one.

22. The compound of claim 2 which is 17aβ-hydroxy-17aα-vinyl-D-homoandrosta-4,16-dien-3-one.

23. A compound of claim 1 wherein there is a double bond in the 1,2 and 4,5 positions.

24. The compound of claim 23 which is 17aβ-acetxoy-D-homoandrosta-1,4,16-trien-3-one.

25. The compound of claim 23 which is 17aβ-hydroxy-17aα-methyl-D-homoandrosta-1,4,16-trien-3-one.

26. A compound of claim 1 wherein there is a double bond in the 1,2 positions.

27. The compound of claim 26 which is 17aβ-acetoxy-D-homoandrosta-1,6-dien-3-one.

28. The compound of claim 1 wherein there is no unsaturation in the A ring.

29. The compound of claim 28 which is 17aβ-hydroxy-D-homo-5α-androst-16-en-3-one.

30. The compound of claim 28 which is 17aβ-hydroxy-17aα-methyl-D-homo-5α-androst-16-en-3-one.

31. The compound of claim 28 which is 1α-methyl-17aβ-tetrahydropyranyloxy-D-homo-5α-androst-16-en-3-one.

32. The compound of claim 28 which is 17aβ-hydroxy-1α-methyl-D-homo-5α-androst-16-en-3-one.

* * * * *